(12) United States Patent
Kane

(10) Patent No.: US 11,179,084 B2
(45) Date of Patent: *Nov. 23, 2021

(54) STIMULATION NEEDLE APPARATUS AND METHOD

(71) Applicant: CIRTEC MEDICAL CORPORATION, Brooklyn Park, MN (US)

(72) Inventor: Lawrence Kane, Roseville, MN (US)

(73) Assignee: CIRTEC MEDICAL CORPORATION, Brooklyn Park, MN (US)

(\*) Notice: Subject to any disclaimer, the term of this patent is extended or adjusted under 35 U.S.C. 154(b) by 135 days.

This patent is subject to a terminal disclaimer.

(21) Appl. No.: 16/367,148

(22) Filed: Mar. 27, 2019

(65) Prior Publication Data

US 2019/0216344 A1 Jul. 18, 2019

Related U.S. Application Data

(63) Continuation of application No. 15/430,061, filed on Feb. 10, 2017, now Pat. No. 10,244,956.

(Continued)

(51) Int. Cl.
*A61N 1/05* (2006.01)
*A61B 5/24* (2021.01)
(Continued)

(52) U.S. Cl.
CPC .............. *A61B 5/24* (2021.01); *A61B 5/6848* (2013.01); *A61M 25/0102* (2013.01);
(Continued)

(58) Field of Classification Search
CPC ............................ A61N 1/0551; A61N 1/3605
See application file for complete search history.

(56) References Cited

U.S. PATENT DOCUMENTS 3,974,834 A 8/1976 Kane
4,230,123 A 10/1980 Hawkins, Jr.
(Continued)

FOREIGN PATENT DOCUMENTS

EP 2497434 9/2012
WO WO 93/14710 8/1993

OTHER PUBLICATIONS

Patent Cooperation Treaty—European Patent Office, Notification of Transmittal of the International Search Report and the Written Opinion of the International Searching Authority, International No. PCT/US2017/017698, dated May 31, 2017, 13 pages.

*Primary Examiner* — Eric D. Bertram
(74) *Attorney, Agent, or Firm* — Haynes and Boone, LLP; J. Andrew Jones; Eric Q. Li

(57) ABSTRACT

In various examples, a stimulation needle apparatus is used for selectively administering a trial stimulation to body tissue of a patient. The stimulation needle apparatus includes a cannula assembly including a cannula and a cannula hub disposed at a proximal cannula end. A stylet assembly includes a stylet sized and shaped to fit within a cannula lumen. A stylet hub is disposed at the proximal stylet end and is configured to engage with the cannula hub. With the stylet hub engaged with the cannula hub, the distal stylet end extends distally from the distal cannula end. A stylet connection is electrically coupled with the stylet and is configured to electrically couple with a stimulator device, such that, a stimulation pulse delivered by the stimulator device is conducted from the stylet connection through the stylet to the distal stylet end to administer the trial stimulation.

20 Claims, 4 Drawing Sheets

Related U.S. Application Data

(60) Provisional application No. 62/294,394, filed on Feb. 12, 2016.

(51) Int. Cl.
*A61M 25/01* (2006.01)
*A61M 25/06* (2006.01)
*A61N 1/36* (2006.01)
*A61B 5/00* (2006.01)

(52) U.S. Cl.
CPC ........... *A61M 25/06* (2013.01); *A61N 1/0551* (2013.01); *A61N 1/3605* (2013.01)

(56) References Cited

U.S. PATENT DOCUMENTS

| | | | | |
|---|---|---|---|---|
| 4,263,547 A * | 4/1981 | Johnson | ................ | H01R 11/18 324/149 |
| 4,266,555 A | 5/1981 | Jamshidi | | |
| 4,861,334 A | 8/1989 | Nawaz | | |
| 5,234,359 A * | 8/1993 | Takahashi | ........... | G01R 1/06788 439/481 |
| 5,279,306 A | 1/1994 | Mehl | | |
| 5,433,739 A * | 7/1995 | Sluijter | ............... | A61B 18/1482 607/113 |
| 5,531,678 A | 7/1996 | Tomba et al. | | |
| 7,274,966 B2 | 9/2007 | Sommer et al. | | |
| 7,643,884 B2 * | 1/2010 | Pond, Jr. | ............. | A61B 17/1757 607/116 |
| 7,711,437 B1 | 5/2010 | Bornzin et al. | | |
| 7,715,925 B2 | 5/2010 | Hafer et al. | | |
| 7,753,696 B2 * | 7/2010 | Hoecke | ................ | H01R 43/22 439/92 |
| 7,763,034 B2 | 7/2010 | Siegel et al. | | |
| 8,147,275 B1 * | 4/2012 | Drake | .................... | H01R 31/06 439/638 |
| 8,332,051 B2 | 12/2012 | Sommer et al. | | |
| 8,382,770 B2 | 2/2013 | DeLegge et al. | | |
| 10,244,956 B2 * | 4/2019 | Kane | ................... | A61N 1/3605 |
| 2004/0230268 A1 * | 11/2004 | Huff | ....................... | A61N 1/056 607/116 |
| 2005/0177199 A1 * | 8/2005 | Hansen | ................ | A61N 1/3752 607/37 |
| 2006/0173521 A1 | 8/2006 | Pond, Jr. et al. | | |
| 2008/0269716 A1 | 10/2008 | Bonde et al. | | |
| 2010/0262158 A1 | 10/2010 | Siegel et al. | | |
| 2010/0317981 A1 * | 12/2010 | Grunwald | ................ | A61B 5/06 600/509 |
| 2011/0208075 A1 | 8/2011 | Giese et al. | | |
| 2012/0232564 A1 * | 9/2012 | Daglow | ............. | A61B 17/3401 606/129 |
| 2014/0121658 A1 * | 5/2014 | Cosman, Jr. | ........ | A61B 18/1477 606/33 |
| 2014/0163655 A1 | 6/2014 | Chitre et al. | | |

* cited by examiner

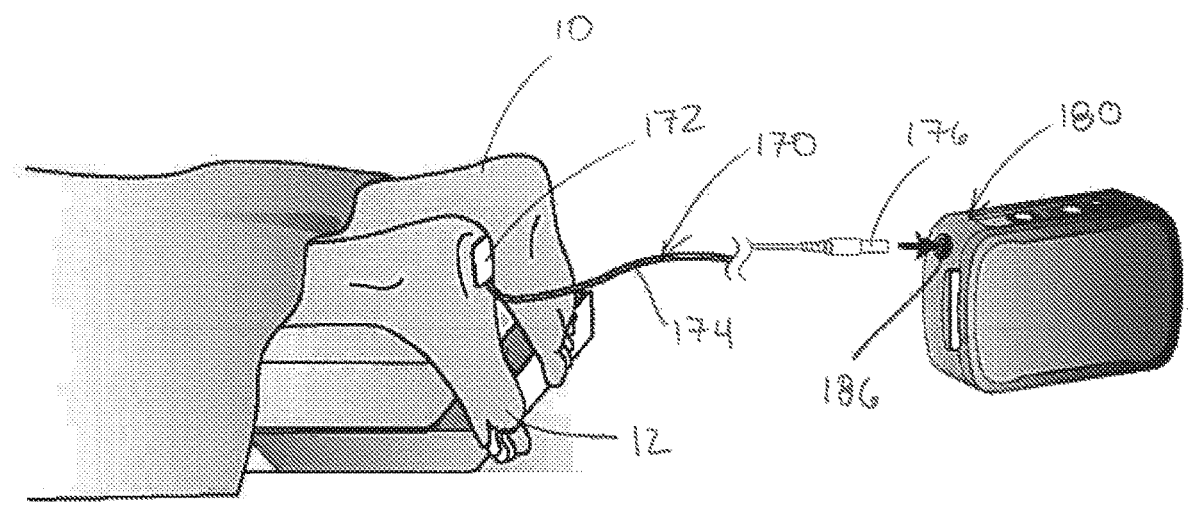
FIG. 6
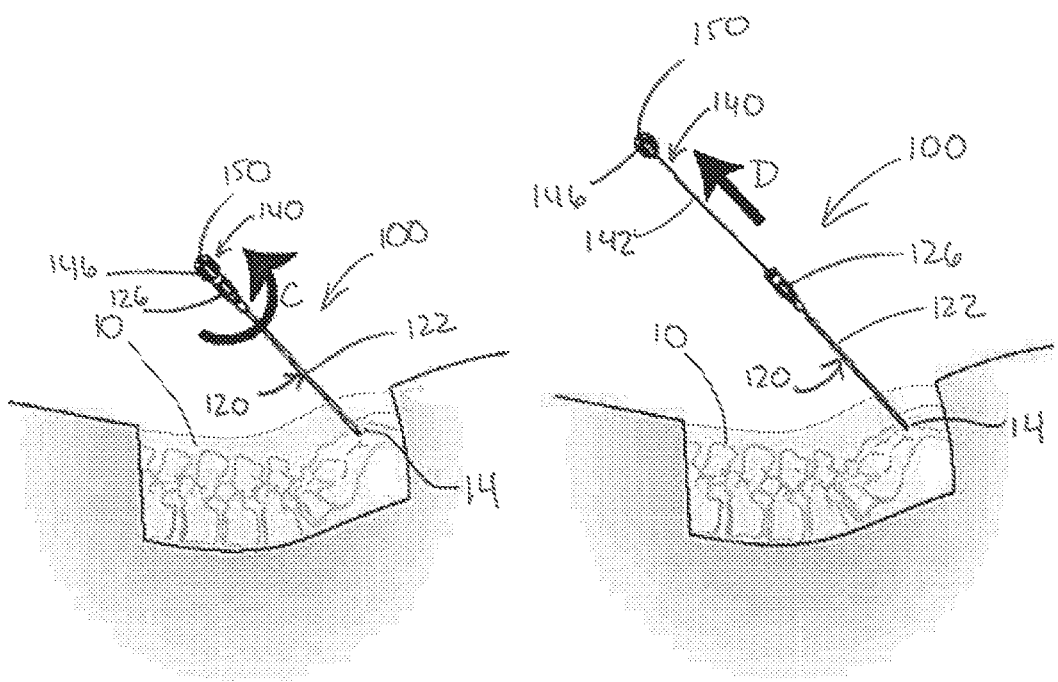
FIG. 7A         FIG. 7B

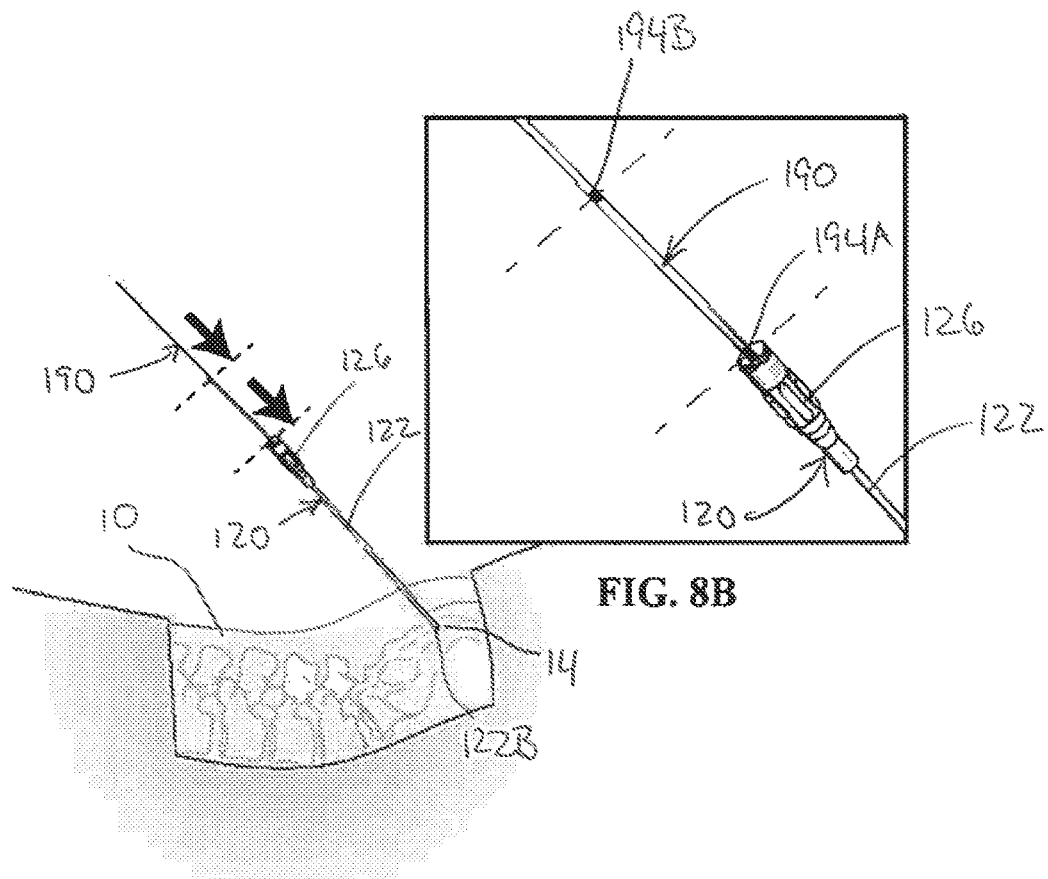
FIG. 8B
FIG. 8A
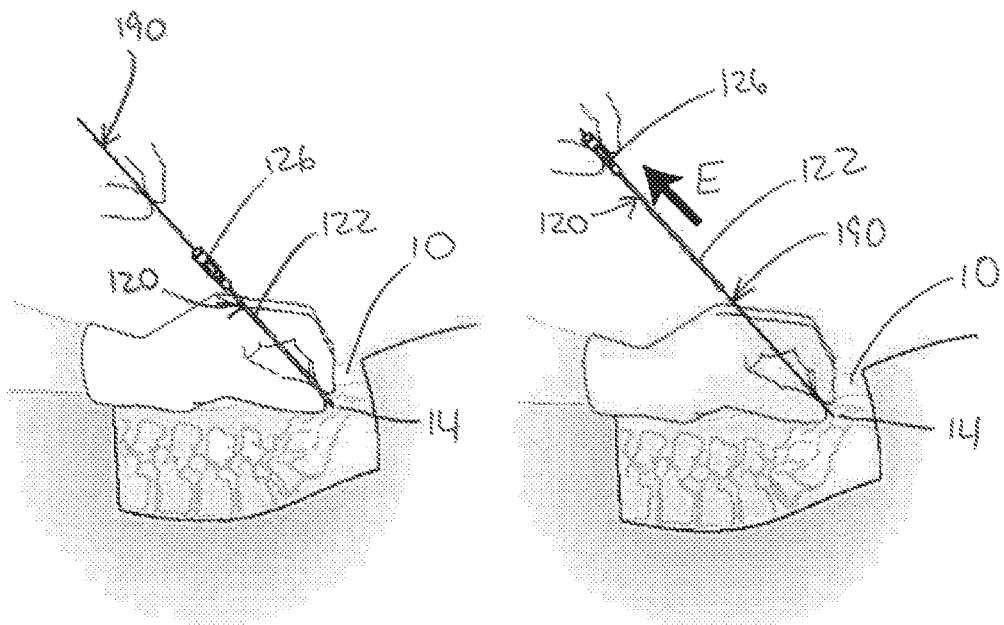
FIG. 9A
FIG. 9B

STIMULATION NEEDLE APPARATUS AND METHOD

PRIORITY DATA

The present application is a Continuation of non-provisional U.S. patent application Ser. No. 15/430,061, filed on Feb. 10, 2017, now issued as U.S. Pat. No. 10,244,956, which is a utility application of provisional U.S. Patent Application No. 62/294,394, filed on Feb. 12, 2016, entitled "STIMULATION NEEDLE APPARATUS AND METHOD," the disclosures of each which is hereby incorporated by reference in their respective entireties.

TECHNICAL FIELD

The present invention relates to a stimulation needle, and more specifically relates to a stimulation needle for performing one or more trial stimulations of a nerve or other body tissue.

BACKGROUND

Previous sacral nerve stimulation needles typically include a stylet removably disposed within a cannula, wherein a stylet hub is press fit or snapped into engagement with a cannula hub to locate the stylet in place within the cannula. A proximal end of the cannula includes a first uninsulated portion (distal from the cannula hub) for temporary attachment to a stimulator device in order to perform trial stimulations in a patient or other subject. The trial stimulations are delivered to the patient or other subject from a second uninsulated portion at a distal end of the cannula, the second uninsulated portion being spaced from the first uninsulated portion.

Previous sacral nerve stimulation needles include several disadvantages. One such disadvantage is with removal of the stylet from within the cannula. In order to remove the stylet, one must grip the cannula with one hand and pull on the stylet hub with the other hand, creating forces in opposing directions (distally and proximally) and potentially causing the cannula to move with respect to the patient or other subject, thereby potentially losing the optimal stimulation position. Another disadvantage of previous sacral nerve stimulation needles is that, by clipping the stimulator device to the proximal end of the cannula for trial stimulations, the overall working length of the needle is decreased because at least the first uninsulated portion at the proximal end of the cannula must be exposed in order to attach the stimulator device to the cannula.

BRIEF DESCRIPTION OF THE DRAWINGS

FIG. 6 is a side perspective view of a ground pad and a stimulation device for use with the stimulation needle apparatus of FIG. 1 to perform a trial stimulation.

FIGS. 7A and 7B are side perspective views of a stimulation needle apparatus in accordance with at least one example of the invention, a stylet assembly being removed from a cannula assembly of the stimulation needle apparatus during a procedure on a patient or other subject.

FIGS. 8A-8B are side perspective views of a directional guide in accordance with at least one example of the invention, the directional guide being inserted into the cannula assembly of FIGS. 7A and 7B during a procedure on a patient or other subject.

FIGS. 9A-9B are side perspective views of the cannula assembly of FIGS. 8A and 8B being removed from the directional guide during a procedure on a patient or other subject.

DETAILED DESCRIPTION

Figure 1:
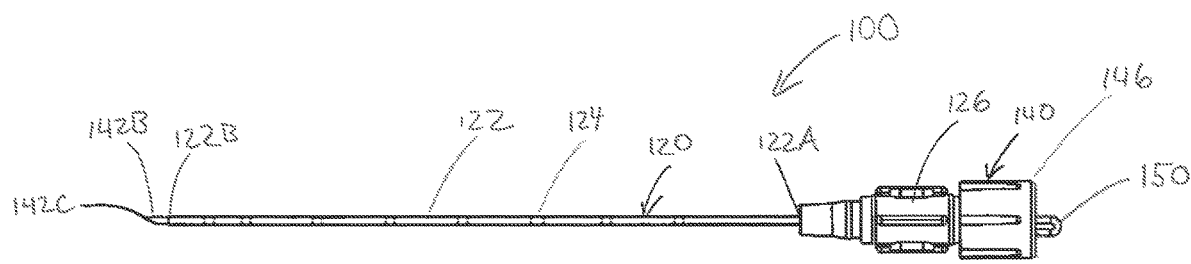
FIG. 1 is a side view of a stimulation needle apparatus in accordance with at least one example of the invention, the stimulation needle apparatus including a stylet assembly engaged with a cannula assembly.
Figure 2:
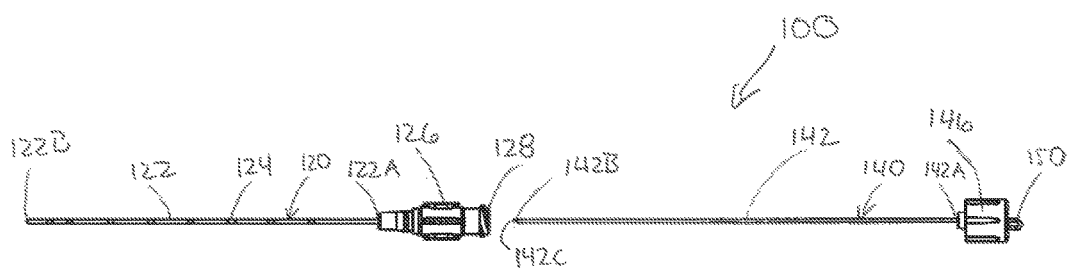
FIG. 2 is an exploded side view of the stimulation needle apparatus of FIG. 1.
Figure 3:
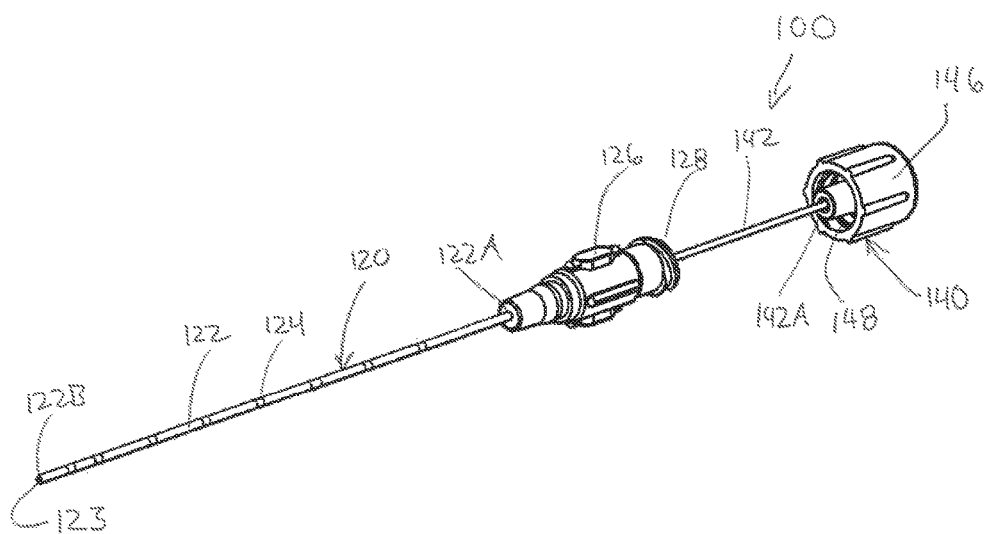
FIG. 3 is a perspective view of the stimulation needle apparatus of FIG. 1 with the stylet assembly partially separated from the cannula assembly.
Figure 4A:
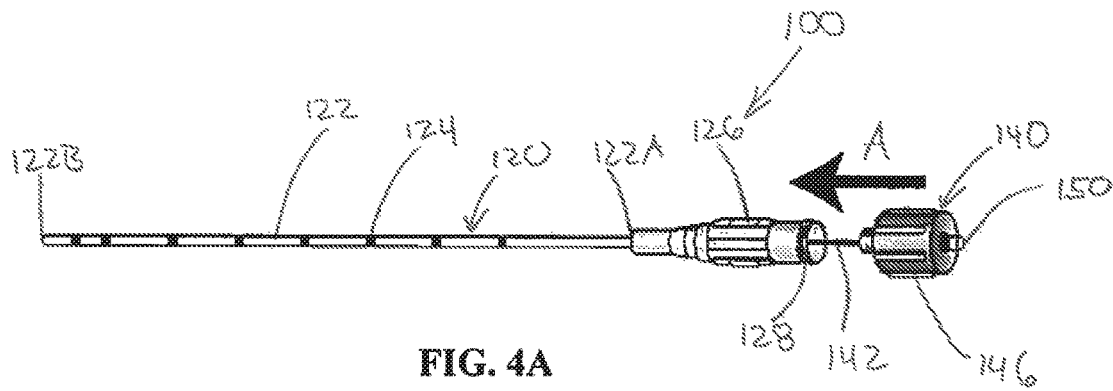
FIG. 4A is a side perspective view of the stimulation needle apparatus of FIG. 1 with the stylet assembly being inserted into the cannula assembly.
Figure 4B:
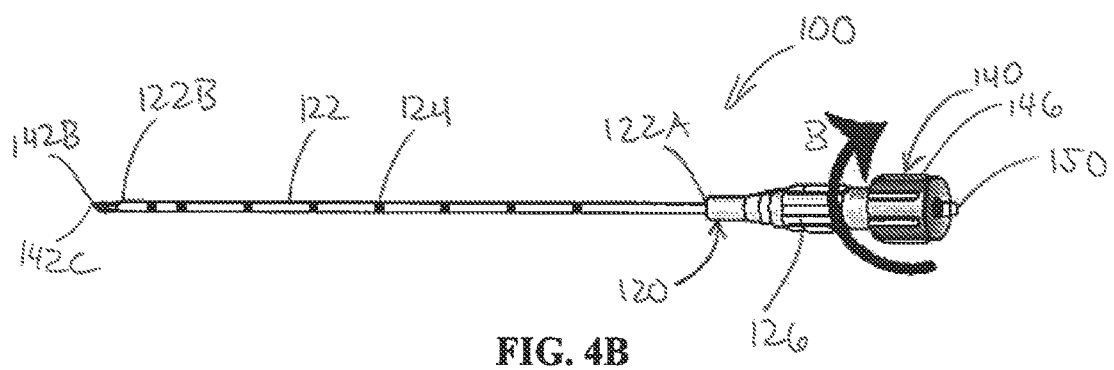
FIG. 4B is a side perspective view of the stimulation needle apparatus of FIG. 1 with the stylet assembly being engaged with the cannula assembly.

Stimulation needles can be used to perform one or more test stimulations at one or more locations within a patient or other subject to assist in locating a proper position for a medical device, such as, for instance, a stimulation lead, within the patient or other subject. The examples of the present invention described herein seek to overcome the shortcomings of the previous sacral nerve stimulation needles.

The present patent application relates to stimulation needle apparatuses and methods. In various examples, as described herein, the stimulation needle is configured to allow for trial stimulations within the patient or other subject in order to determine an optimal or otherwise desirable location for an implantable device, such as, but not limited to, a stimulation lead, within the patient or other subject.

Although described with respect to positioning proximate and performing trial stimulations with respect to a sacral nerve, it should be understood that the present invention can be used with other nerves and/or body tissue and/or to position various types of medical devices within the patient or other subject.

Referring to FIGS. 1-4B, in some examples, a stimulation needle apparatus 100 is configured to access body tissue of a patient 10 or other subject (see FIGS. 6-9B). In some examples, the stimulation needle apparatus 100 is configured to selectively administer a trial stimulation to the body tissue of the patient 10 or other subject. In some examples, the stimulation needle apparatus 100 includes a cannula assembly 120 and a stylet assembly 140 removably coupled with the cannula assembly 120. The stimulation needle apparatus 100, in some examples, is configured to pierce, puncture, or otherwise extend through body tissue in order to be positioned at a desired location within the patient 10 or other subject. In some examples, the stimulation needle apparatus 100 is configured to be inserted through body tissue and through a sacral foramen in order to access a sacral nerve with the stimulation needle apparatus 100.

In some examples, the cannula assembly 120 includes a cannula 122. In some examples, the cannula 122 includes a tubular shape having a cannula lumen 123 extending from a proximal cannula end 122A to a distal cannula end 122B.

The cannula 122, in some examples, is insulated. For instance, in some examples, the cannula 122 is formed from one or more insulative materials. In other examples, the cannula 122 is formed by one or more conductive materials and coated, covered, or otherwise including one or more insulative materials disposed on an exterior surface of the cannula 122. In this way, in various examples, the cannula 122 is configured to insulate the body tissue of the patient 10 or other subject from a stimulation pulse conducted within the cannula.

In some examples, the cannula assembly 120 includes a cannula hub 126 disposed at the proximal cannula end 122A. In some examples, the cannula lumen 123 is accessible through the cannula hub 126. In further examples, the cannula hub 126 can include a passage therein with access to the cannula lumen 123. That is, in some examples, an opening at the proximal cannula end 122A is open and accessible through a proximal end of the cannula hub 126, for instance, to allow fluid communication through the cannula hub 126 to the cannula lumen 123. In some examples, the cannula hub 126 is engaged with the cannula 122. For instance, in an example, the cannula hub 126 is molded onto the cannula 122. In another example, the cannula hub 126 is integrally formed with the cannula 122. For instance, the entire cannula assembly 120, in some examples, can be molded.

In some examples, the cannula 122 includes one or more depth marks 124 on an exterior surface of the cannula 122. In some examples, the depth marks 124 are printed on the cannula 122. In some examples, the depth marks 124 are etched, molded, or otherwise formed into the cannula 122, either instead of or in addition to being printed on the cannula 122. The one or more depth marks 124, in some examples, can be used to determine a depth at which the cannula 122 and, in turn, the stimulation needle apparatus 100 are inserted into the patient 10 or other subject, as will be described in more detail herein. In some examples, the one or more depth marks 124 can be used to determine a depth of insertion of the stimulation needle apparatus 100.

In some examples, the stimulation needle apparatus 100 includes a stylet assembly 140. In some examples, the stylet assembly 140 includes a stylet 142 sized and shaped to fit within the cannula lumen 123. In some examples, the stylet 142 includes a proximal stylet end 142A and a distal stylet end 142B. The stylet assembly 140, in some examples, includes a stylet hub 146 disposed at the proximal stylet end 142A. In some examples, the stylet hub 146 is configured to engage with the cannula hub 126. In some examples, the stylet hub 146 engages with the cannula hub 126 with a twist engagement. For instance, in some examples, the stylet hub includes one or more stylet threads 148 configured to mateably engage with one or more cannula threads 128 of the cannula hub 126. For instance, in some examples, referring specifically to FIGS. 4A and 4B, the stylet 142 can be inserted within the cannula 122 and the stylet assembly 140 moved distally with respect to the cannula assembly 120 along a direction A and rotated along a direction B to engage the one or more cannula threads 128 with the one or more stylet threads 148 (FIG. 3), thereby engaging the stylet hub 146 with the cannula hub 126. To disengage, the stylet assembly 140 can be rotated in a direction opposite to direction B and the stylet assembly 140 moved proximally with respect to the cannula assembly 120 along a direction opposite to direction A.

Such a configuration allows for engagement and disengagement of the stylet assembly 140 and the cannula assembly 120 using relative rotational motion. In this way, the likelihood of the cannula assembly 120 migrating proximally or distally during engagement or disengagement of the stylet assembly 140 and the cannula assembly 120 is reduced because the forces imparted to the stylet assembly 140 and/or the cannula assembly 120 for engagement or disengagement of the stylet assembly 140 and the cannula assembly 120 are largely rotational and largely not directed longitudinally (proximally or distally) with respect to the stylet assembly 140 and/or the cannula assembly 120. Although threaded engagement between the stylet assembly 140 and the cannula assembly 120 is shown, in other examples, other types of rotational engagement are contemplated, such as, but not limited to, a tab-in-slot connection, a bayonet connection, and a compression coupling. In other examples, non-rotational engagement of the stylet assembly 140 and the cannula assembly 120 can be used, such as, for instance, a press fit configuration and/or a snap-together configuration.

The stylet 142, in some examples, is electrically conductive to allow an electrical pulse to be conducted along the stylet 142. In some examples, the stylet is formed from a metallic material. In some examples, the distal stylet end 142B includes a pointed tip 142C. In some examples, the pointed tip 142C is configured to pierce, puncture, or otherwise pass through tissue, for instance, to insert the stylet 142 within a patient 10 or other subject. In some examples, with the stylet hub 146 engaged with the cannula hub 126, the distal stylet end 142B extends distally from the distal cannula end 122B. In further examples, the pointed tip 142C extends distally from the distal cannula end 122B with the stylet hub 146 engaged with the cannula hub 126, for instance, to facilitate piercing, puncturing, or otherwise passing through tissue, for instance, to insert the stimulation needle apparatus 100 within a patient 10 or other subject.

In some examples, the stylet apparatus 140 includes a stylet connection 150 electrically coupled with the stylet 142. In some examples, the stylet connection 150 is disposed at a proximal portion of the stylet hub 146 and configured to electrically couple with a stimulator device 180 (see FIG. 5A). Having the stylet connection 150 disposed proximal to the stylet hub 146 is an improvement over the conventional designs described above having first and second spaced-apart uninsulated portions, both distal the stylet hub. With the present design, there is more effective length of the stylet 142. In some examples, with the stimulator device 180 electrically coupled to the stylet connection 150, a stimulation pulse delivered by the stimulator device 180 is conducted from the stylet connection 150 through the stylet 142 to the distal stylet end 142B to administer the trial stimulation to the patient 10 or other subject. In some examples, the stylet connection 150 extends proximally from the stylet hub 146. In some examples, the stylet connection 150 includes a loop. In some examples, the stylet connection 150 is integrally formed with the stylet 142. For example, the stylet 142 can extend through the stylet hub 146 and proximally from the stylet hub 146 to form the stylet connection 150, such that the stylet 142 and the stylet connection 150 are integrally formed from the same piece of material. In other examples, the stylet connection 150 can be electrically coupled to the stylet 142 with a conductor disposed between the stylet connection 150 and the stylet 142. In some examples, the conductor can include a wire or other conductive member. In some examples, the conductor can include a material different from the material or materials from which at least one of the stylet 142 and the stylet connection 150 are formed.

Figure 5A:
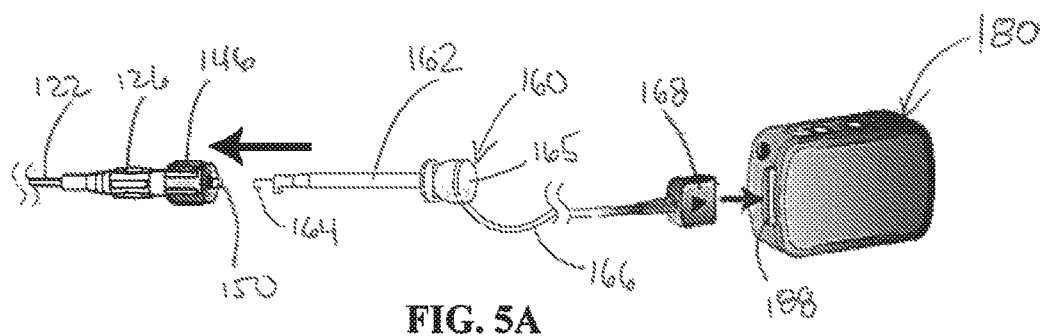
FIGS. 5A and 5B are side perspective views of a connector and a stimulation device for use with the stimulation needle apparatus of FIG. 1 to perform a trial stimulation.
Figure 5B:
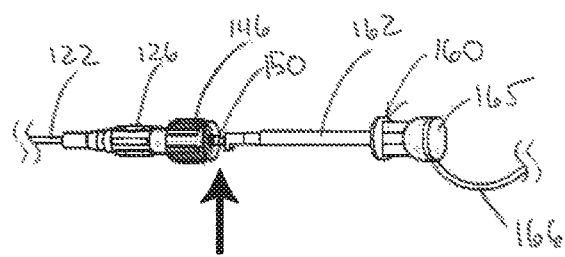

Referring to FIGS. 5A and 5B, in some examples, the stylet connection 150 is configured to be selectively coupled to a connector 160, such as, but not limited to a test clip 160. In other examples, a connector other than a test clip can be used, such as an alligator clip, a pin and socket connector, a threaded connector, or the like. In some examples, the test clip 160 includes a body 162 with a conductive hook 164 extendable from the body 162. For instance, the conductive hook 164 can be extended from within the body 162 (by pushing button 165, for instance) (FIG. 5A) and then attached to the stylet connector 150 (FIG. 5B). With the test clip 160 attached to the stylet connector 150, the test clip 160 can be electrically coupled to the stimulator device 180. In some examples, the test clip 160 includes a wire 166 for electrically coupling the test clip 160 to the stimulator device 180. In some examples, the wire 166 includes a plug 168 or other connector for coupling to a socket 188 or other mating connector of the stimulator device 180. In other examples, the wire 166 is configured to couple to at least one intermediate device between the test clip 160 and the stimulator device 180. For instance, in an example, the wire 166 includes a pin or other connector configured to couple with a trial connector or other device which, in turn, is coupled to the stimulator device 180.

Referring to FIG. 6, in some examples, a ground device 170 can be attached to the patient 10, for instance, on the heel of a foot 12, in order to complete the circuit to allow for a trial stimulation to be administered. In some examples, the ground device 170 includes a ground pad 172 configured to be adhered or otherwise placed in contact with skin of the patient 10. In some examples, the ground device 170 further includes a wire 174 extending from the ground pad 172, the wire 174 including a plug 176 or other connector for mateably engaging with a socket 186 or other connector of the stimulation device 180 in order to electrically couple the ground device 170 with the stimulation device 180.

Once the ground device 170 is attached to the patient 10 and coupled to the stimulator device 180 and the stimulation needle apparatus 100 is in position within the patient 10 and electrically coupled to the stimulation device 180, in some examples, a trial stimulation can be delivered. In some examples, the cannula 122 is insulated to inhibit the stimulation pulse of the trial stimulation from being conducted to the body tissue radially outwardly through the cannula 122. In this way, the stimulation pulse is conducted from the stylet connection 150 through the stylet 142 to the distal stylet end 142B to administer the trial stimulation from the distal stylet end 142B to body tissue of the patient (for instance, the location 14 in FIG. 7A). In some examples, the stimulation needle apparatus 100 is intended to be inserted proximate nerve tissue of the patient 10 or other subject. In further examples, the stimulation needle apparatus 100 is intended to be inserted proximate a sacral nerve of the patient 10 or other subject.

Once the trial stimulation is administered, the patient 10 or other subject is monitored for a response to the trial stimulation to determine whether the stimulation needle apparatus 100 is properly placed with respect to the body tissue. In some examples, if the stimulation needle apparatus is at the correct location within the patient 10 (for instance, a location 14 in FIG. 7A), a particular response should be noted by a physician or other caregiver performing the procedure. In some instances, toe movement, for example, could be an indicator that the stimulator needle apparatus 100 is properly positioned within the patient 10. Other responses, either in addition to or instead of toe movement, can indicate proper positioning of the stimulation needle apparatus 100, depending on what area or what tissue (nerve tissue, for instance) is being targeted. In some examples, an imaging technique (such as fluoroscopy, for instance) can be used instead of or in addition to verify proper positioning of the stimulation needle apparatus 100 within the patient 10. If the proper response from the patient 10 or other subject is not obtained with the trial stimulation or if it is otherwise evident that the stimulation needle apparatus 100 is not properly located within the patient 10 or other subject, in some examples, the stimulation needle apparatus 100 can be repositioned within the patient 10 or other subject and another trial stimulation can be performed (and/or image taken). This process can be repeated, in some examples, until the proper positioning of the stimulation needle apparatus 100 is obtained.

Once proper positioning is achieved, in some examples, the stylet assembly 140 can be removed from the cannula assembly 120. In some examples, removing the stylet 142 from within the cannula 122 includes disengaging the stylet hub 146 from the cannula hub 126. In some examples, the stylet hub 146 is disengaged from the cannula hub 126 by twisting the stylet hub 146 out of engagement with the cannula hub 126. For instance, referring to FIGS. 7A and 7B, in some examples, once the stimulation needle apparatus 100 is positioned at the desired location (for instance, the location 14), the stylet assembly 140 can be rotated in direction C with respect to the cannula assembly 120 to disengage the stylet assembly 140 from the cannula assembly 120. Once disengaged, in some examples, the stylet assembly 140 can be moved proximally with respect to the cannula assembly 120 along direction D to remove the stylet assembly 140 from the cannula assembly 120, thereby leaving the cannula assembly 120 in place within the patient 10. As described above, the likelihood of the cannula assembly 120 migrating proximally or distally during disengagement of the stylet assembly 140 from the cannula assembly 120 is reduced because the forces imparted to the stylet assembly 140 and/or the cannula assembly 120 for disengagement of the stylet assembly 140 and the cannula assembly 120 are largely rotational and largely not directed longitudinally (proximally or distally) with respect to the stylet assembly 140 and/or the cannula assembly 120. In this way, in some examples, the stylet 142 can be removed from within the cannula 122 while maintaining the location of the cannula 122 within the patient 10 or other subject.

Referring to FIGS. 8A and 8B, in some examples, once the stylet assembly 140 is removed from the cannula assembly 120, a directional guide 190 can be inserted. In some examples, the directional guide 190 includes a guidewire. In some examples, the directional guide 190 includes one or more markings 194 to assist in positioning the directional guide 190 with respect to the cannula assembly 120. For instance, in some examples, the directional guide 190 can include a first marking 194A for placement just proximal of a proximal end of the cannula assembly 140 to indicate that a distal end of the directional guide 190 is positioned at the distal cannula end 122B and, in turn, at the location 14 within the patient 10. In some examples, the directional guide 190 can include a second marking 194B for use with another cannula assembly, such as a cannula assembly with a longer cannula than the cannula 122 of the cannula assembly 120. The one or more markings 194, in some examples, allow for a visual indication that the directional guide 190 is in the proper location with respect to the cannula assembly 120 to decrease the chance that the directional guide 190 is extended distally too far with respect to the cannula assembly 120 such that the distal end of the directional guide 190 extends beyond the distal cannula end 122B and, in turn, beyond the location 14 within the patient 10. In some examples, the one or more markings 194 can also allow for a visual indication that the directional guide 190 is in the proper location with respect to the cannula assembly 120 to decrease the chance that the directional guide 190 has not been inserted far enough into the cannula assembly 120 such that the distal end of the directional guide 190 is left within the cannula 122 of the cannula assembly 120 and short of the location 14 within the patient 10.

Referring to FIGS. 9A and 9B, once the directional guide 190 is inserted within the cannula assembly 120 such that the distal end of the directional guide 190 is positioned at the location 14 of the patient 10, the cannula assembly 120 can be removed from the directional guide 190. For instance, in some examples, the physician or other caregiver can hold the directional guide 190 in place with respect to the patient 10 or other subject while removing the cannula assembly 120 along a direction E. With the cannula assembly 120 removed, in various examples, another component can then be inserted within the patient 10 or other subject, for instance, over the directional guide 190, such as, but not limited to a dilator assembly, an over-the-wire lead assembly, or the like.

The present inventors have recognized various advantages of the subject matter described herein. For instance, in some examples, the stimulation needle apparatus provides for the ability to administer a trial stimulation to a location within a patient in order to determine if the stimulation needle apparatus is properly placed with respect to the location. Additionally, in some examples, the stimulation needle apparatus includes a stylet connection at a proximal end of the stimulation needle apparatus to provide a relatively easily accessible connection point for electrically coupling a stimulation device to the stylet in order to administer the trial stimulation. Also, in some examples, the stimulation needle apparatus includes a stylet assembly that is able to be removed from engagement with the cannula assembly with little to no movement of the cannula assembly with respect to the patient or other subject. While various advantages of examples of stimulation needle apparatuses and methods are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A stimulation needle apparatus, comprising:
   a stylet assembly that includes:
      a stylet that extends along a longitudinal axis, wherein the stylet has a proximal stylet end and a distal stylet end;
      a stylet hub located at the proximal stylet end; and
      a conductive loop that is integrally formed from a same piece of material as the stylet, wherein the conductive loop is electrically coupled to the stylet, thereby defining a two-dimensional enclosure, wherein the conductive loop is configured to engage with a stimulator device, such that an electrical pulse generated by the stimulator device can propagate to the stylet through the conductive loop, and wherein an entirety of the conductive loop extends proximally beyond a planar surface of the stylet hub.

2. The stimulation needle apparatus of claim 1, wherein the conductive loop is configured to be hooked onto an alligator clip, a pin and socket connector, or a threaded connector of the stimulator device.

3. The stimulation needle apparatus of claim 1, further comprising a cannula assembly that is engageable with the stylet assembly.

4. The stimulation needle apparatus of claim 3, wherein the cannula assembly and the stylet assembly are engaged via an engagement mechanism selected from the group consisting of: a threaded engagement, a tab-in-slot connection, a bayonet connection, and a compression coupling.

5. The stimulation needle apparatus of claim 3, wherein the stylet assembly is configured to:
   engage with the cannula assembly via a first rotational motion; and
   disengage with the cannula assembly via a second rotational motion opposite the first rotational motion.

6. The stimulation needle apparatus of claim 5, wherein the first rotational motion and the second rotational motion are relative to the longitudinal axis and are applied at least in part via the stylet hub.

7. The stimulation needle apparatus of claim 3, wherein an engagement between the stylet assembly and the cannula assembly is non-rotational.

8. The stimulation needle apparatus of claim 7, wherein the stylet assembly and the cannula assembly are engaged using a press fit configuration or a snap-together configuration.

9. The stimulation needle apparatus of claim 3, wherein the cannula assembly includes:
   a cannula that defines a cannula lumen extending along the longitudinal axis from a proximal cannula end to a distal cannula end; and
   a cannula hub disposed at the proximal cannula end, wherein the cannula lumen is accessible through the cannula hub.

10. The stimulation needle apparatus of claim 9, wherein the stylet is sized and shaped to fit within the cannula lumen.

11. The stimulation needle apparatus of claim 9, wherein the cannula includes one or more depth marks.

12. The stimulation needle apparatus of claim 11, wherein the one or more depth marks are etched or molded into the cannula.

13. The stimulation needle apparatus of claim 9, wherein the cannula is electrically insulated.

14. A stimulation needle apparatus, comprising:
   a stylet assembly that includes:
      a stylet that extends along a longitudinal axis, wherein the stylet has a first end and a second end opposite the first end;
      a stylet hub located at the first end; and
      a conductive loop that is coupled to the stylet hub in a manner such that an entirety of the conductive loop extends proximally beyond a planar surface of the stylet hub, thereby defining a two-dimensional enclosure, and wherein the conductive loop is configured to engage with a stimulator device, such that an electrical pulse generated by the stimulator device can propagate to the stylet through the conductive loop, wherein the conductive loop and the stylet are integrally formed from a same piece of material, and wherein the conductive loop is configured to be hooked onto an alligator clip, a pin and socket connector, or a threaded connector of the stimulator device.

15. The stimulation needle apparatus of claim 14, further comprising a cannula assembly that is engageable with the stylet assembly via an engagement mechanism selected from the group consisting of: a threaded engagement, a tab-in-slot connection, a bayonet connection, and a compression coupling.

16. The stimulation needle apparatus of claim 15, wherein the stylet assembly is configured to:
   engage with the cannula assembly via a first rotational motion; and
   disengage with the cannula assembly via a second rotational motion opposite the first rotational motion;
   wherein the first rotational motion and the second rotational motion are relative to the longitudinal axis and are applied at least in part via the stylet hub.

17. The stimulation needle apparatus of claim 15, wherein the stylet assembly and the cannula assembly are engaged using a press fit configuration or a snap-together configuration.

18. The stimulation needle apparatus of claim 15, wherein the cannula assembly includes:
   a cannula that defines a cannula lumen extending along the longitudinal axis from a proximal cannula end to a distal cannula end; and
   a cannula hub disposed at the proximal cannula end, wherein the cannula lumen is accessible through the cannula hub;
   wherein:
   the stylet is sized and shaped to fit within the cannula lumen;
   the cannula includes one or more depth marks etched or molded into the cannula; and
   the cannula is electrically insulated and includes one or more depth marks.

19. A stimulation needle apparatus, comprising:
   a stylet assembly that includes:
      a stylet that extends along a longitudinal axis, wherein the stylet has a proximal stylet end and a distal stylet end;
      a stylet hub located at the proximal stylet end; and
      a conductive mechanism whose entirety thereof extends proximally beyond a planar surface of the stylet hub, wherein the conductive mechanism is a single piece of structure, such that the single piece of structure and the planar surface of the stylet hub collectively define a two-dimensional enclosure, wherein the conductive mechanism is configured to be attachable to a clip or a connector, and wherein the conductive mechanism is electrically coupled to the stylet and configured to engage with a pulse generator, such that an electrical pulse generated by the pulse generator can propagate to the stylet through the conductive mechanism.

20. The stimulation needle apparatus of claim 19, wherein the conductive mechanism consists of a U-shaped conductive loop.

* * * * *